United States Patent [19]

Fitzgerald

[11] 4,019,499
[45] Apr. 26, 1977

[54] COMPRESSION IMPLANT FOR URINARY INCONTINENCE

[75] Inventor: Martin Bruce Fitzgerald, Santa Barbara, Calif.

[73] Assignee: Heyer-Schulte Corporation, Goleta, Calif.

[22] Filed: Apr. 22, 1976

[21] Appl. No.: 679,250

[52] U.S. Cl. .......................... 128/1 R; 128/DIG. 25
[51] Int. Cl.² ...................................... A61B 19/00
[58] Field of Search ............ 128/1 R, DIG. 25, 346; 3/1

[56] References Cited

UNITED STATES PATENTS

| | | | |
|---|---|---|---|
| 2,649,854 | 8/1953 | Salm | 128/1 R |
| 3,646,929 | 3/1972 | Bonnar | 128/1 R |
| 3,789,828 | 2/1974 | Schulte | 128/1 R |
| 3,903,894 | 9/1975 | Rosen et al. | 128/346 |

*Primary Examiner*—Lawrence W. Trapp
*Attorney, Agent, or Firm*—Donald D. Mon

[57] ABSTRACT

A compression implant to resist the flow of urine through the urethra comprising a cap, an external planar pressure face on the cap, a base, an external bearing face on the base, and a peripheral wall continuously interconnecting the cap and the base. A peripheral fold in the peripheral wall enables the face to move toward and away from the base by changing the shape of the fold without elastic stretching of the material which forms the wall. The cap, base and peripheral wall together define an internal cavity which can be filled with an adjustably variable amount of fluid whereby to adjust the firmness of the capsule and thereby to adjust the force which it exerts against the urethra after implantation.

12 Claims, 4 Drawing Figures

U.S. Patent    April 26, 1977    4,019,499
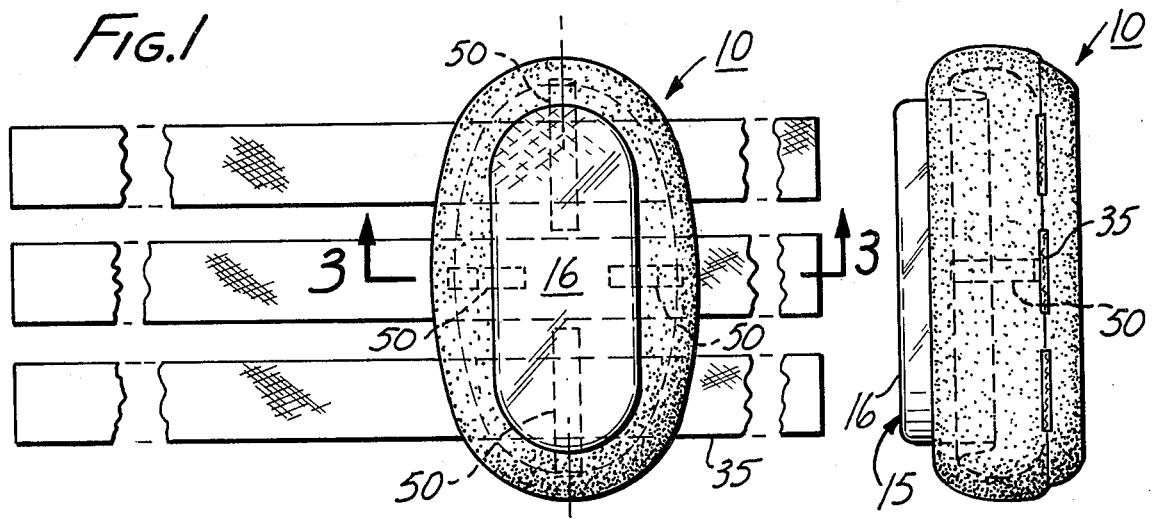
FIG.1
FIG.2
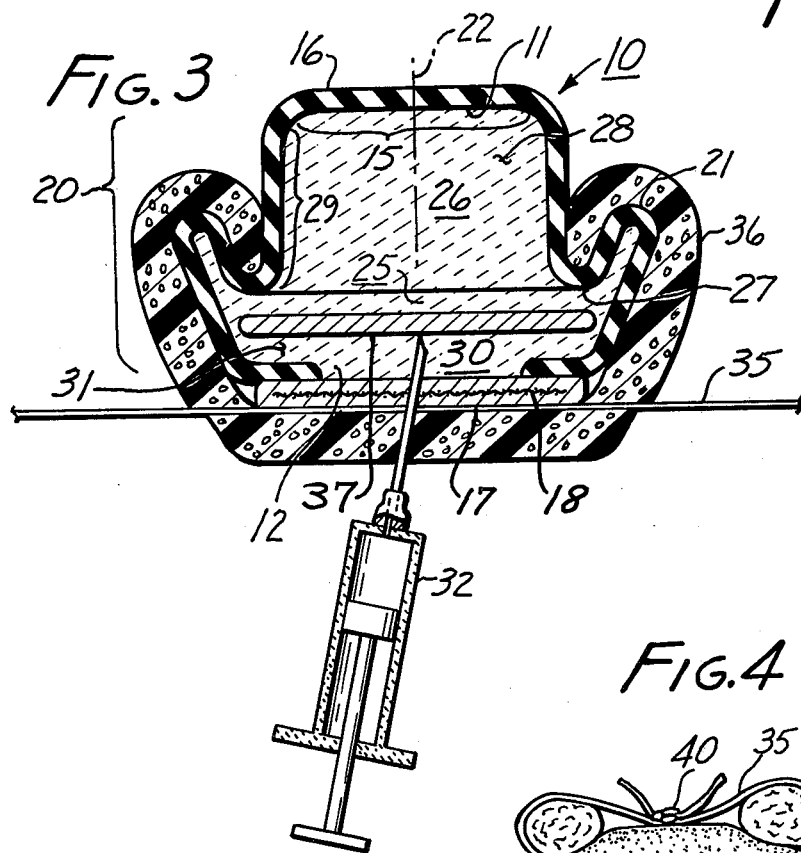
FIG.3
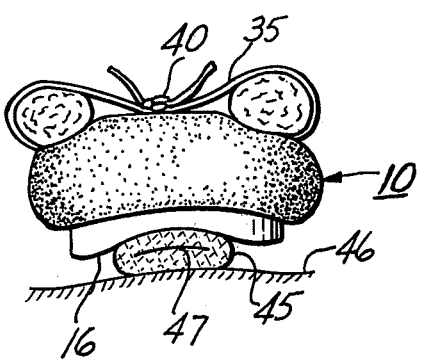
FIG.4

COMPRESSION IMPLANT FOR URINARY INCONTINENCE

This invention relates to a compression implant which is implantable in the human body between supporting structure and the urethra to press the urethra to a flow-resisting condition.

Urethral incontinence prostheses are known. For example, one such prothesis is shown in Schulte U.S. Pat. No. 3,789,828, issued Feb. 5, 1974, which has the same intended function as the present invention. Although the said Schulte device has performed ably, still its generally curvilinear, domed pressure face tends to permit the urethra to roll off of it or, considered otherwise, to permit it to roll away from the urethra, especially when the prothesis is made firmer by injection of additional fluid into it. A problem in the Schulte device is that addition of fluid to make the device firmer also causes it to approach a spherical configuration which makes it even more difficult to maintain a stable contact between the urethra and the prosthesis. Therefore, there is a direct relationship between the firmness and the ability of the device to remain in continuous firm contact with the urethra.

It is an object of this invention to provide a compression implant to be placed between supporting structure and the urethra so as to compress the urethra and tend to close it. The prothesis can be overcome, and flow of urine through the urethra can be caused, by muscular contraction of the bladder producing a sufficient pressure in the urethra to open the lumen to flow. It is desirable to be able to adjust the firmness of the implant whereby to determine the pressure needed to overcome the prosthesis, but without changing the basic shape of the pressure face of the implant. The implant of this invention can maintain a substantially planar pressure face, with varying amounts of fluid within the implant, so as to vary its firmness and pressure against the urethra. This reduces the risk that the urethra and the implant may roll apart from one another, thereby terminating the function of the implant.

An implant according to this invention comprises a cap, an external pressure face on the cap, a base, an external bearing face on the base, a peripheral wall which continuously interconnects the cap and the base, and a fold in the wall which enables the face to move toward and away from the base by changing the shape of the fold without stretching the material which forms the wall. The cap the base, and the peripheral wall together define an internal cavity. The cap is preferably relatively shape-retaining, although somewhat flexible, and is nominally planar. On the base side of the fold, the cavity is open to receive fluid-like material, such as a gel, or saline solution, or both to impart a desired firmness to the device by adjusting the volume of the material in it. The gel or other fluid-like material has little or no shear strength, and behaves in a substantially hydraulic manner, although it is preferably sufficiently viscous that it resists too easy parallel shear-like movement between the cap and the base.

According to a preferred but optional feature of the invention, the cap includes a cup-like depression which is contiguous to the remainder of the cavity and which receives a flexible and resilient material, such as a semi-cured silicone rubber, so as to provide additional firmness for the cap, when the cap is formed of a relatively flexible elastomeric skin.

The above and other features of this invention will be fully understood from the following detailed description and the accompanying drawings, in which:

FIG. 1 is a plan view of the presently preferred embodiment of the invention;

FIG. 2 is a right-hand view of FIG. 1;

FIG. 3 is a cross-section taken at line 3—3 of FIG. 1; and

FIG. 4 shows the implant in place in the human body in contact with the urethra.

In FIG. 1 there is shown a compression implant 10 according to the invention. This is also the best mode. The implant is preferably made with a skin 11 which can conveniently be a membrane of medical grade silicone rubber. It can be formed by dipping an appropriately shaped plug into liquid uncured silicone rubber until the desired thickness is built up, and then curing it. A window 12 is cut in the bottom so that the cured skin can be peeled off the plug leaving the configuration shown in FIGS. 1, 2 and 3. A wall thickness on the order of 0.008 inch is suitable, and the material may be the conventional medical grade silicone rubber sometimes called "Silastic".

The implant includes a cap 15 having an external pressure face 16 which is substantially planar. The implant also includes a base 17 which may be a patch of silicone rubber with a fabric-reinforcement 18 cast therein. It is cemented to the remainder of the skin at the window to close the window.

The implant also includes a peripheral wall 20 which extends downwardly from the cap and upwardly from the base so as to interconnect them and to form a continuous fluid-tight construction. The peripheral wall includes peripheral fold 21, which is shown in FIG. 3. It is preferably re-entrant, although it will be understood that it could, if desired, simply be any other class of fold, such as a simple crease or accordian-type fold. A folded construction is sometimes called a "pleat". The fold is shape-retaining, but distortable, so as to permit the cap and base to move apart along an axis 22, still maintaining the parallelism between the pressure face and the base. The cap, therefore, moves rather like a plunger. The wall is thick enough and may be reinforced by a fabric reinforcement (not shown) cast in it or applied to its surface to withstand pressure which would tend to expand the wall. The change of shape when fluid is added or removed is therefore primarily that of movement of the cap and base toward and away from each other.

The cap and its pressure face are resiliently flexible and tend to be shape-retaining. The face is sufficiently soft that it is indentable by the urethra, but tends to return to its planar configuration. Because the relatively thin cap skin will not usually have this property, the skin must either be made thicker adjacent to the pressure face, or it must be reinforced. Preferably a portion of the cavity 25 formed inside the skin is filled with material of different firmness and other properties to provide the reinforcement.

For example, in the upper portion 26 of the cavity contiguous to the pressure face, and preferably extending down as far as the inside edge 27 of the fold, there is a filler 28 of resilient material, such as medical grade silicone rubber, which has been cured to such a degree that it tends to remain in place and is resiliently deformable. This gives flexural strength and lateral firmness relative to the axis to the portion of the cavity bounded by wall 29 and the cap 15, and this portion may move up and down rather like a plunger relative to the base.

The lower portion 30 of the cavity is filled to any desired amount with a fluid-like material 31, such as a silicone rubber gel, which is cured to a lesser degree of firmness than filler 28. It has little resistance to shear and can flow as a viscous fluid. The implant will customarily be manufactured by underfilling it with an amount of material 31, using only an amount sufficient to bring the internal volume of the implant up to a minimum amount needed for implantation. This permits, either before or after implantation, the use of a syringe 32 to inject more fluid, such as a sterile saline solution, into the lower portion 30 to bring the implant up to the desired degree of firmness by insertion of fluid. In so doing, the inherent strength of the walls themselves will tend to cause the cap to move upwardly and thereby to exert a greater upward force should it be retained in the same position. This is to say that by inserting more saline solution, a greater force can be caused to be exerted by the pressure after the device is installed. If the amount of material in the device is too great, and the prosthesis must be softened, material is withdrawn instead of added. In both situations, the pressure face remains planar.

A plurality of flexible ties 35 or a single wide tie of a suitable cloth-like material such as Dacron is provided for assisting the implantation of the device. A covering of an opencell, porous, foam-like material, such as silicone rubber or polyurethane foam 36, covers most of the surface of the implant, excluding the pressure face, to enable tissue to grow into the interstices and finally hold the implant in place. A needle stop 37 comprising a plate of sufficiently hard material to resist needle puncture provides for limiting the depth of penetration of the needle.

Initially, the implant will be held in place as shown in FIG. 4, wherein the ties, acting as a sling, are sutured in the male patient into the heavy Bucks fascia of the penis, rather than being supported by the wrapping of a strap around the urethra. In this manner, undesirable pressure necrosis is avoided. As shown in the aforesaid Schulte patent, the prosthesis will be located at the crus of the penis in the bulbocavernosus. The bands are brought under the ischiocavernosus and are tied or sutured in a joinder 40. The tension produced in the ties is directly reflected in the firmness of the support of the prosthesis, and generally they will be held quite strongly. They bear against the base, and the base is supported strongly by them. Also, over a period of time, tissue will grow around the device so as to support it in place.

The urethra 45 which is pressed against surrounding tissue 46 tends to have its lumen 47 closed by this pressure. As can best be seen in FIGS. 1 and 4, the pressure face is substantially planar. Because of the relatively stiff flexibility of the cap, the pressure face remains substantially planar but is somewhat indentible by the urethra over a relatively wide range of firmnesses. The firmness, and thus the amount of indentation can be determined by varying the amount of fluid-like material in the lower portion of the cavity 30. This invention thereby overcomes some of the disadvantages of the Schulte device. The firmness is adjustable without giving rise to concern that the urethra will "roll off" of the pressure face.

Radio opaque markers 50 are formed in the base and the peripheral wall to enable the surgeon to visualize the location and configuration of the implant after implantation in the patient, and also to locate the needle when it is inserted into the implanted device from outside the skin when the firmness of the device is to be adjusted.

Suitable approximate external dimensions in inches for the prosthesis inside the foam layer are as follows:

|  | Small | Medium | Large |
| --- | --- | --- | --- |
| Length | 1.08 | 1.20 | 1.50 |
| Width | 0.89 | 0.95 | 1.06 |
| Normal Height | 0.99 | 1.06 | 1.11 |

This invention is not to be limited by the embodiment shown on the drawings and described in the description which is given by way of example and not of limitation, but only in accordance with the scope of the appended claims.

I claim:

1. A compression implant to resist flow of urine through the urethra comprising: a flexible cap; and external pressure face on the cap; a base; a peripheral wall continuously interconnecting the cap and the base; a peripheral fold in the peripheral wall enabling the face to move toward and away from the base by changing the shape of the fold without stretching the material which forms the wall; the cap, base and peripheral wall defining an internal cavity; fluid-like material in the cavity including the portion of the cavity contiguous to the base, whereby the spacing apart of the face and base can be determined by selection of the amount of said fluid-like material in the cavity, and the resistance of the cap to force exerted on the pressure face which tends to move it toward the base can similarly be determined.

2. An implant according to claim 1 in which a filler material is placed in the cavity within the cap to reinforce the pressure face against deformation, said reinforced pressure face being resiliently indentable.

3. An implant according to claim 2 in which the pressure face is substantially planar.

4. An implant according to claim 3 in which the fold is a re-entrant pleat.

5. An implant according to claim 3 in which the materail of at least a portion of the implant is self-sealing against leakage of said fluid after puncture by and withdrawal of an injection needle.

6. An implant according to claim 2 in which the filler material is cured silicone gel, and in which the material in the cavity contiguous to the base is a gel.

7. An implant according to claim 6 in which the pressure face is substantially planar.

8. An implant according to claim 3 in which the base and at least part of the wall are covered by an open-celled foam.

9. An implant according to claim 8 in which radio opaque markers are carried by the implant.

10. An implant according to claim 8 in which a needle stop is placed in the cavity to limit the penetration of a needle.

11. An implant according to claim 9 in which a needle stop is placed in the cavity to limit the penetration of a needle.

12. An implant according to claim 1 in which a needle stop is placed in the cavity to limit the penetration of a needle.

* * * * *